United States Patent [19]

Weinstock et al.

[11] 4,051,144
[45] Sept. 27, 1977

[54] SINISTER-3,5-DISUBSTITUTED OXOZOLIDINES THEIR PREPARATION AND USE

[75] Inventors: Leonard M. Weinstock, Belle Mead; Roger J. Tull, Metuchen; Dennis M. Mulvey, Whitehouse, all of N.J.

[73] Assignee: Charles E. Frosst & Co., Kirkland, Canada

[21] Appl. No.: 529,314

[22] Filed: Dec. 4, 1974

Related U.S. Application Data

[60] Continuation of Ser. No. 283,875, Aug. 25, 1972, abandoned, which is a division of Ser. No. 172,234, Aug. 16, 1972, Pat. No. 3,718,647, which is a division of Ser. No. 818,474, April 21, 1969, Pat. No. 3,657,237.

[51] Int. Cl.$^2$ .......................................... C07D 263/04
[52] U.S. Cl. ............................................. 260/307 FA
[58] Field of Search .................................. 260/307 FA

[56] References Cited

U.S. PATENT DOCUMENTS 2,964,530  12/1960  Zenitz ................................. 260/307
3,160,634  12/1964  Hodge ................................. 260/307

OTHER PUBLICATIONS

Bergmann et al. C.A. 15, 3277–3279 (1921).

Primary Examiner—Donald G. Daus
Assistant Examiner—D. B. Springer
Attorney, Agent, or Firm—Daniel T. Szura; Harry E. Westlake, Jr.

[57] ABSTRACT

Preparation of S-3-X-4-(3-substituted amino-2-hydroxypropoxy)-1,2,5-thiadiazole beta adrenergic blocking agents using as starting material an optically active alkalmine in the sinister configuration, or a derivative of said alkalmine, which is reacted with an 3-X-4-chloro(or RO–where R is hydrogen or an alkali metal)-1,2,5-thiadiazole. Certain 3-morpholino-4-chloro(or RO-)-1,2,5-thiadiazoles and certain alkamines and their preparation also are described. Preferred alkamines are S-3,5-disubstituted oxazolidines.

17 Claims, No Drawings

SINISTER-3,5-DISUBSTITUTED OXOZOLIDINES THEIR PREPARATION AND USE

This is a continuation, of application Ser. No. 283,875 filed. Aug. 25, 1972, now abandoned which in turn is a division of application Ser. No. 172,234, filed Aug. 16, 1972, now U.S. Pat. No. 3,718,647, issued Feb. 27, 1973, which in turn is a division of Ser. No. 818,474, filed Apr. 21, 1969, now U.S. Pat. No. 3,657,237, issued Apr. 18, 1972.

This invention is concerned with a novel and commercially feasible method for preparing the biologically active, S-enantiomer of a 3-X-4-(3-substituted amino-2-hydroxypropoxy)-1,2,5-thiadiazole product. Substantially all of the biological activity of these products resides in the S-enantiomer which was obtained by other workers by the resolution of the racemic product or by the resolution of intermediates employed in their synthesis. These prior methods offer several disadvantages, principally the need to use cyanogen for the synthesis of the intermediate 3-chloro-4-hydroxy-1,2,5-thiadiazole, an important intermediate, as well as the need to resolve the 3-X-4-(3-substituted amino-2-hydroxypropoxy)-1,2,5-thiadiazole derivative thereof. It is well known that resolution procedures are uneconomical as they provide low yields of active material because half of the yield of racemic product formed is of no value, and at least some of the desired isomer is not recoverable by feasible large scale procedures.

This invention therefore is concerned principally with the preparation of optically active 3-X-4-(3-substituted amino-2-hydroxypropoxy)-1,2,5-thiadiazoles utilizing in the synthesis thereof derivatives of optically active carbohydrates thus avoiding all of the difficulties encountered by other workers in the resolution of the end product itself or the need to resolve racemic compounds at any stage of the synthesis of the active end products, or the need to employ cyanogen in the synthesis of the thiadiazole starting material.

According to the principal process of this invention a 1,2,5-thiadiazole, structure I, is reacted with an optically active alkamine of the sinister (S) configuration, structure II, to provide product III in the sinister configuration. Either structure I compound or structure II compound contains a reactive hydroxyl group or an alkali metal salt thereof, thus the reaction can be illustrated by the following scheme:

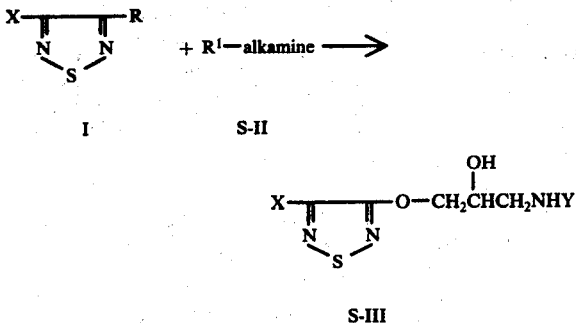

wherein either R or $R^1$ is the reactive hydroxyl group or an alkali metal salt thereof wherein the alkali metal preferably is sodium or potassium. When $R^1$ is HO— or (alkali metal-O—) then R is chloro; when R is OH or a salt thereof, then $R^1$ is the sulfonate derivative of the alkamine. X in the above structures represents chloro, lower alkyl having 1 to 3 carbon atoms, lower alkoxy having from 1 to 3 carbon atoms, phenyl, benzyl, morpholino, piperidyl, hydroxypiperidyl, and N-lower alkyl piperazinyl; and Y is a straight or branched chain lower alkyl having from 1 to 5 carbon atoms which is optionally hydroxy substituted.

When in the foregoing reaction scheme R in the thiadiazole I is chloro then the $R^1$-alkamine is an (S)-oxazolidine of the structure

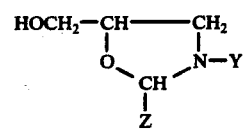

wherein Y has the meaning assigned above and Z is the residue of any known aldehyde; any one of which can be employed in the synthesis of the oxazolidine.

When R in the thiadiazole reactant I is hydroxy, then the hydroxyl group of the $R^1$-alkamine is activated by forming a leaving group, i.e., an easily displaceable group, such as a sulfonate of the aforementioned oxazolidines.

When R in compound I is chloro and $R^1$ in compound II represents the reactive hydroxyl group, the optically active product, S-III, is prepared by the reaction of the thiadiazole I and the S-alkamine, S-II, in the presence of a strong base. The reaction preferably is carried out at ambient temperature although the reaction mixture either can be heated up to reflux temperature if desired, or cooled to 0° C. A solvent for the reactants is desirable and any conventional solvent can be employed for this purpose; suitable ones being polar aprotic solvents such as dimethylformamide (DMF), dimethyl sulfoxide (DMSO), tetrahydrofuran (THF), hexamethylphosphoramide (HMP); lower alkanols and the like. The readily available and relatively inexpensive tert-butanol has been found to be a quite suitable, general purpose solvent for these intermediates. Strong bases that are recommended for use in the reaction are alkali metal alkoxides or alkali metal hydroxides preferably the sodium or potassium alkoxides or hydroxides, or sodium hydride. When product S-III in the form of the free base is obtained as an oil, crystalline material can be prepared by forming the salt by known methods. Suitable salts are those formed with mineral acids or organic acids such as for example the hydrochloride salt, the sulfate salt, the hydrogen maleate salt or other desired mineral or organic acid salt.

When R in compound I represents the reactive hydroxyl group or the alkali metal salt thereof and $R^1$ is an activated hydroxyl group, the reagents are coupled advantageously by combining the reactants in the presence of a solvent to form the desired product, S-III. Heating the reaction mixture up to the reflux temperature can be employed if desired and any of the usual organic solvents can be used, especially suitable ones being polar aprotic solvents, such as DMF, DMSO, THF, HMP, lower $C_{1-5}$ alkanols and the like.

The $R^1$-alkamines of the sinister configuration, S-II, can be prepared by a novel method that constitutes another feature of this invention.

The S-oxazolidines are prepared by the reaction of S-1,2-dihydroxy-3-amino(or substituted amino) propane or the S-1-sulfonyloxy-2-hydroxy-3-amino(or substituted amino)-propane with any aldehyde, ZCHO, to provide an S-oxazolidine of the structure

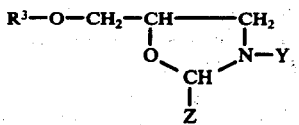

wherein R³ is hydrogen or the sulfonyl group. The aldehyde used in the preparation of the oxazolidine is not critical as any aldehyde aldehydes, be used in the formation of the lower alkyl structure which subsequently is cleaved by hydrolysis to remove the

grouping provided by the aldehyde. For practical purposes any commercially available and inexpensive aldehyde can be employed and among these there can be mentioned aliphatic aldehydes, alicyclic, aromatic or heterocyclic aldehydes such as lower aldehydes, benzaldehyde, phenyl-lower alkyl aldehydes, and the like, the phenyl moiety of either of the latter aldehydes optionally having one or more similar or dissimilar substituents selected from halogen, lower alkyl, halo alkyl, amino, acylamino, mono- or di-alkylamino, nitro, alkoxy, phenalkoxy, haloalkoxy and hydroxy, a heterocyclic aldehyde optionally having substituents as halogen, lower alkyl, phenalkyl and the like. Among the many aldehydes that can be employed there can be mentioned acetaldehyde, propionaldehyde, butyraldehyde, phenylacetaldehyde, anisaldehyde, benzaldehyde, mesitaldehyde, tolualdehyde, furfural and the like. As mentioned above, R³ can be hydrogen or an alkyl-, aryl- or aralkylsulfonate. The activated hydroxyl group is prepared by reaction with any known and particularly any commercially available sulfonyl halide. As any sulfonyl halide will activate the hydroxyl group and as the sulfonyl moiety is subsequently removed it is not critical that any particular sulfonyl halide be employed to form the sulfonyloxy derivative of the S-1,2-dihydroxy-3-amino(or substituted amino)-propane. For practical purposes, commercially available and inexpensive sulfonyl halides would be employed for this purpose and these would fall into the class of alkylsulfonyl halides and benzenesulfonyl halides wherein the benzene moiety can optionally be substituted with one or more similar or dissimilar substituents selected from lower alkyl, lower alkoxy, halo, amino and nitro substituents. Among the commercially available sulfonyl halides that can be employed for this purpose there can be mentioned methanesulfonyl chloride, benzenesulfonyl chloride, nitrobenzenesulfonyl chloride, bromobenzenesulfonyl chloride, chlorobenzenesulfonyl chloride, toluenesulfonyl chloride, toluenesulfonyl fluoride, trichlorobenzenesulfonyl chloride, tribromobenzenesulfonyl chloride, fluorobenzenesulfonyl chloride, 4-chloro-2(or 3)-nitrobenzenesulfonyl chloride, hexadecanesulfonyl chloride, 2-mesitylenesulfonyl chloride, methoxybenzenesulfonyl chloride and the like.

The S-1,2-dihydroxy-3-amino(or substituted amino)-propane employed as starting substance can be made in a single step and in quite good yield by the reductive alkylation of the selected amine with glyceraldehyde. The success of this process was not predictable from the prior art that teaches that glyceraldehyde cyclizes in the presence of base. It was found, however, that reductive alkylation can be effected by hydrogenating a mixture of the selected amine, glyceraldehyde and a hydrogenation catalyst. Hydrogenation advantageously is carried out under a pressure from about 1 to about 10 atmospheres. Any solvent can be employed, suitable ones being tetrahydrofuran, methanol, a mixture of benzene and methanol and the like. Suitable catalysts are platinum, Raney nickel and palladium. While for the present invention one employs an amine of the structure $YNH_2$ and D-glyceraldehyde, it will be appreciated that any amine such as ammonia, a primary or secondary amine, or a nitrogen-containing heterocycle of the structure $$\bigcirc NH$$

can be reductively alkylated with glyceraldehyde by the novel method of this invention.

The S-1,2-dihydroxy-3-amino(or substituted amino)-propane having an activated hydroxyl group is prepared by reaction with any known and particularly any commercially available sulfonyl halide such as those identified above.

Preparation of
S-3-X-4-[3-(Y-amino)-2-hydroxypropoxy]-1,2,5-thiadiazole via 3-X-4-chloro-1,2,5-thiadiazole

EXAMPLE 1

Step A: Preparation of S(—)-glycolamine

A mixture of tert-butylamine (37.44 g.; 0.513 mole), methanol (150 ml.) and 5% palladium-on-carbon (1.0 g.) is shaken in a hydrogenation bomb under three atmospheres hydrogen pressure. A solution of D-glyceraldehyde (15 g.) in methanol (60 ml.) is added over a one hour period during hydrogenation. After the addition, the mixture is shaken for an additional 15 hours. The catalyst is removed by filtration and the solvent evaporated in vacuo yielding S(—)-1,2-dihydroxy-3-tert-butylaminopropane [S(—)-glycolamine] in the form of an oil which is crystallized by trituration with ether to give 11.0 g. (45%) yield of product, m.p. 80°–82° C. $[\alpha]_D$ −30.1 (1N aqueous HCl).

Step B: Preparation of S-3-tert-butyl-5-hydroxymethyloxazolidine

A mixture of S(—)-glycolamine (29.4 g.; 0.2 mole), aqueous formaldehyde (20 ml. of 37% solution) and benzene (80 ml.) is heated under reflux with continuous removal of water for two hours. The solvent then is evaporated in vacuo (15 mm. pressure) and the oily residue distilled, b.p. 80°–82° C., (0.5 mm. pressure) providing 29.9 g. (94%) S-3-tert-butyl-5-hydroxymethyloxazolidine.

Step C: Preparation of 3-morpholino-4-chloro-1,2,5-thiadiazole 3,4-Dichloro-1,2,5-thiadiazole (100.0 g.; 0.645 mole) is added dropwise over a 30-minute period at 105°–110° C. to morpholine (224 ml.; 2.58 mole). After the addition, the mixture is stirred 2 hours at 105°–110° C., then cooled to 15° C. and quenched with water (250 ml.). This mixture then is made acidic with concentrated hydrochloric acid (250 ml.) whereupon an insoluble oil soon crystallizes to a heavy solid mass. After crystallization is complete the solid is filtered and washed with water and then dried at 35° C. in vacuo yielding 125.5 g. (95%) of 3-morpholino-4-chloro-1,2,5-thiadiazole, m.p. 43°–45° C.

Step D: Preparation of S(—)-3-morpholino-4-(3-tert-butylamino-2-hydroxypropoxy)-1,2,5-thiadiazole and its hydrogen maleate salt A mixture of 3-morpholino-4-chloro-1,2,5-thiadiazole (2.05 g.; 10 mmole), S-3-tert-butyl-5-hydroxymethyloxazolidine (10 mmole) and potassium tert-butoxide in tert-butanol (11.7 ml. of 0.885 N, 10 mmole) is stirred at 25° C. for 16 hours. The solvent then is evaporated in vacuo and the residue treated with 20 ml. of 1N hydrochloric acid. The mixture is heated at 65° C. for one-half hour, cooled to 25° C. and extracted with ether. The aqueous layer is made alkaline with potassium carbonate and extracted with ether. The extracts are washed with water, dried and evaporated to an oily residue of S(—)-3-morpholino-4-(3-tert-butylamino-2-hydroxypropoxy)-1,2,5-thiadiazole. This oil in 10 ml. of tetrahydrofuran is converted to the crystalline hydrogen maleate salt by treatment with an equivalent amount of maleic acid by the procedure described in Example 1, Step B, to provide a 30% yield of S(—)-3-morpholino-4-(3-tert-butylamino-2-hydroxypropoxy)-1,2,5-thiadiazole hydrogen maleate.

By replacing the maleic acid employed in the above procedure by hydrochloric acid, sulfuric acid, tartaric acid or any other desired acid the corresponding acid salt is formed. When sulfuric acid is employed in the ratio of 1 mole of acid to 2 moles of thiadiazole the sulfate salt of S(—)-3-morpholino-4-(3-tert-butylamino-2-hydroxypropoxy)-1,2,5-thiadiazole is obtained, m.p. 253.5°–254° C. $[\alpha]_{405}$ —13.8° [C = 1, 1N, HCl].

By replacing morpholine in Step C with an equivalent quantity of N-methylpiperazine, piperidine and 4-hydroxypiperidine and then following substantially the same methods of Steps C and D there is obtained, respectively, the 3-(4-methylpiperazinyl)-, 3-piperidyl-, and 3-(4-hydroxypiperidyl)- analogs.

By replacing the tert-butylamine employed in Step A by an equivalent quantity of isopropylamine, 2,2-dimethylpropylamine, and 1,1-dimethyl-2-hydroxyethylamine and following substantially the same procedures described in Steps A-D there is obtained s-(—)-3-morpholino-4-[3-(Y-amino)-2-hydroxypropoxy]-1,2,5-thiadiazole compounds wherein Y is isopropyl, 2,2-dimethylpropyl, and 1,1-dimethyl-2-hydroxyethyl, respectively.

EXAMPLE 2

Step A: Preparation of S-2-isopropyl-3-tert-butyl-5-hydroxymethyloxazolidine

A mixture of S(—)-glycolamine (10 g.; 68 mmole) in freshly distilled isobutyraldehyde (50 ml.) is heated under reflux with continuous removal of water for 2 hours. The solvent then is removed in vacuo and the oily residue distilled. A forerun of 0.85 g. of material with b.p. 70°–75° C. (0.1 mm. pressure) is obtained which is 98% pure S-2-isopropyl-3-tert-butyl-5-hydroxymethyloxazolidine when analyzed by vapor pressure chromatography (vpc).

Step B: Preparation of S(—)-3-morpholino-4-(3-tert-butylamino-2-hydroxypropoxy)-1,2,5-thiadiazole and its hydrogen maleate salt This product is obtained in 35% yield by following the procedure described in Example 1, Step D, with the exception that 10 mmole of S-2-isopropyl-3-tert-butyl-5-hydroxymethyloxazolidine is substituted for the oxazolidine employed in Example 1, Step D.

EXAMPLE 3

Step A: Preparation of S-2-phenyl-3-tert-butyl-5-hydroxymethyloxazolidine

A mixture of S(—)-glycolamine (20 g.; 0.136 mole), benzaldehyde (50 ml.; 288 mmole) and benzene (30 ml.) is heated under reflux for 8 hours while removing the water as formed into a Dean Stark trap filled with benzene. The temperature of the reaction mixture is maintained at 110°–113° C. over the entire period. The benzene is removed in vacuo (15 mm. pressure) and the excess benzaldehyde is removed by distillation at 0.1 mm. pressure. The residual oil (31.9 g.; 99% yield) is 90% pure S-2-phenyl-3-tert-butyl-5-hydroxymethyloxazolidine by vpc and can be used directly in the next step. If desired, the oxazolidine can be distilled (105°–108° C.; 0.002 mm. pressure) to provide 96% pure product.

Step B: Preparation of S(—)-3-morpholino-4-(3-tert-butylamino-2-hydroxypropoxy)-1,2,5-thiadiazole and its hydrogen maleate salt The above product is prepared in 50% yield by the process described in Example 1, Step D, except 10 mmole of S-2-phenyl-3-tert-butyl-5-hydroxymethyloxazolidine is substituted for the oxazolidine employed in Example 1, Step D.

Any other aldehyde, particularly (though not necessarily) any of the commercially available aldehydes identified hereinabove can be reacted with an S-1,2-dihydroxy-3-amino(or substituted amino)propane or an S-1-sulfonyloxy-2-hydroxy-3-amino(or substituted amino)propane by the method illustrated in Step B of Example 1 or Step A of Examples 2 or 3, to provide the desired oxazolidine which then can be reacted with the appropriate 1,2,5-thiadiazole by the procedure of Example 1, Step D or Example 4, Step B, to give product S-III.

EXAMPLE 4

Step A: Preparation of S-3-tert-butyl-5-(benzenesulfonyloxymethyl)oxazolidine

To a solution of S-3-tert-butyl-5-hydroxymethyloxazolidine (1.59 g.; 10 mmole), prepared as described in Example 1, Step B, in pyridine (3 ml.) there is added benzenesulfonyl chloride (10 mmole) and the mixture stirred for about 1 hour at 25° C. Ether (20 ml.) is added whereupon S-3-tert-butyl-5-(benzenesulfonyloxymethyl)oxazolidine hydrochloride is precipitated, removed by filtration and washed well with ether and dried in vacuo at 40° C.

The same oxazolidine product is obtained by replacing the S(—)-glycolamine employed in Example 1, Step B, by an equivalent quantity of S-1-benzenesulfonyloxy-2-hydroxy-3-tert-butylaminopropane and then following substantially the same procedure described in Step B of Example 1.

By replacing the benzenesulfonyl chloride employed in Step A by 10 mmole of p-tolylsulfonyl chloride, p-nitrobenzenesulfonyl chloride, and p-bromobenzenesulfonyl chloride there is obtained respectively:

S-3-tert-butyl-5-(p-toluenesulfonyloxymethyl)oxazolidine, m.p. 143.5°–145° C., yield 83.5%
S-3-tert-butyl-5-(p-nitrobenzenesulfonyloxymethyl)-oxazolidine, yield 98%
S-3-tert-butyl-5-(p-bromobenzenesulfonyloxymethyl)-oxazolidine, m.p. 118°–120° C. yield 95%

By replacing the benzenesulfonyl chloride by an equivalent quantity of methylsulfonyl chloride and/or other lower alkylsulfonyl chloride, p-chlorophenylsulfonyl chloride, or any other sulfonyl halide, particularly (though not necessarily) any of the commercially available sulfonyl halides identified hereinabove in the process illustrated in Step A of this example for reaction with any desired S-5-hydroxymethyloxazolidine provides the sulfonyloxy derivatives thereof which upon reaction with the appropriate 1,2,5-thiadiazole according to Step B of this example gives product S-III.

Step B: Preparation of S(—)-3-morpholino-4-(3-tert-butylamino-2-hydroxypropoxy)-1,2,5-thiadiazole hydrogen maleate S-3-tert-butyl-5-(benzenesulfonyloxymethyl)oxazolidine (10 mmole) is dissolved in benzene (12 ml.) and tetrahydrofuran (0.9 ml.). The sodium salt of 3-morpholino-4-hydroxy-1,2,5-thiadiazole (10 mmole) is added and the mixture refluxed for 16 hours. The reaction mixture then is extracted with three 10 ml. portions of 1N hydrochloric acid and the aqueous layer then made alkaline with ammonia and extracted with three 10 ml. portions of benzene. The combined benzene extracts are dried and evaporated to give S(—)-3-morpholino -4-(3-tert-butylamino-2-hydroxypropoxy)-1,2,5-thiadiazole. This product is converted to the hydrogen maleate salt by treatment with maleic acid in tetrahydrofuran by substantially the same procedure described in Example 1, Step D, to provide a 32% yield of S(—)-3-morpholino-4-(3-tert-butylamino-2-hydroxypropoxy)-1,2,5-thiadiazole hydrogen maleate.

By replacing the S-3-tert-butyl-5-(benzenesulfonyloxy-methyl)oxazolidine employed in Step B by an equimolecular quantity of S-3-tert-butyl-5-(p-toluenesulfonyloxymethyl)oxazolidine, S-3-tert-butyl-5-(p-nitrobenzenesulfonyloxymethyl)-oxazolidine, and S-3-tert-butyl-5-(p-bromobenzenesulfonyloxymethyl)-oxazolidine and following substantially the same procedure described in Step B above there is obtained the free base and the hydrogen maleate salt of S(—)-3-morpholino-4-(3-tert-butylamino-2-hydroxypropoxy)-1,2,5-thiadiazole in substantially the same yield.

By replacing the 3-morpholino-4-hydroxy-1,2,5-thiadiazole employed in Step B of Example 4 by an equivalent quantity of the following 1. 3-chloro-4-hydroxy-1,2,5-thiadiazole or its alkali metal salt,
2. 3-ethyl-4-hydroxy-1,2,5-thiadiazole or its alkali metal salt,
3. 3-ethoxy-4-hydroxy-1,2,5-thiadiazole or its alkali metal salt,
4. 3-phenyl-4-hydroxy-1,2,5-thiadiazole or its alkali metal salt,
5. 3-benzyl-4-hydroxy-1,2,5-thiadiazole or its alkali metal salt, and following substantially the same procedure described in Step B of Example 4, there is obtained respectively, the S-3-chloro-, S-3-ethyl-, S-3-ethoxy-, S-3-phenyl-, and S-3-benzyl-4-(3-tert-butylamino-2-hydroxypropoxy)-1,2,5-thiadiazole.

The S-3-X-4-[3-(Y-amino)-2-hydroxypropoxy]-1,2,5-thiadiazole compounds prepared by the process of this invention as well as their salts have been found to exhibit β-adrenergic blocking properties and are thus useful in the management of angina pectoris. Because of this property the optically active products are useful for the control of tachycardia that may be drug induced (as by isoproterenol) or brought about by physiological conditions.

The optically active products particularly in the form of their salts can be prepared in pharmaceutical formulations suitable for oral or parenteral administration and also can be combined with other active ingredients for simultaneous administration. No special problems are involved in preparing suitable formulations of the optically active compounds or salts thereof and methods generally employed for this purpose, which are known to those skilled in this art, are entirely suitable. Dosage units of from about 2 mgs. to about 10 mgs. can be provided for the symptomatic admustment of dosage of the optically active substances by the physician depending upon the age and condition of the patient.

Illustrative examples of suitable pharmaceutical compositions containing S(—)-3-morpholino-4-(3-tert-butylamino-2-hydroxypropoxy)-1,2,5-thiadiazole hydrogen maleate as active ingredient follow. Each of the compositions are prepared by conventional methods, and the quantities recited are for each unit dosage. The other optically active products prepared as hereinbefore described can be similarly formulated.

| Injectable Solution | |
| --- | --- |
| Active Compound | 1 mg. |
| Sodium chloride | 9 mgs. |
| Distilled water q.s. | 1.0 ml. |
| Capsules | |
| Active Compound | 5 mgs. |
| Magnesium stearate | 2.0 mg. |
| Lactose U.S.P. | 19.3 mg. |

What is claimed is:

1. An optically active oxazolidine in the sinister configuration having the structure:

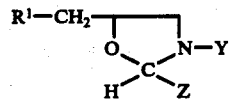

wherein $R^1$ is hydroxy or $R^3O$— wherein $R^3$ is $C_{1-16}$ alkylsulfonyl, benzenesulfonyl optionally having substituents selected from the group consisting of
 a. an amino group,
 b. 1-3 bromo groups,
 c. 1-3 chloro groups,
 d. a chloro and a nitro group,
 e. a fluoro group,
 f. a methoxy group,
 g. 1-3 methyl groups and
 h. a nitro group;

Z is hydrogen, benzyl, $C_1$-$C_3$ alkyl, phenyl optionally having substituents selected from the group consisting of
 a. 1-3- bromo groups,
 b. 1-3 chloro groups,
 c. 1-3 methyl groups,
 d. a methoxy group and
 e. 1-3 hydroxy groups, or Z can be furfuryl; and Y is a straight or branched chain $C_1$-$C_5$ alkyl or hydroxy substituted straight or branched chain $C_1$-$C_5$ alkyl.

2. An oxazolidine as claimed in claim 1 wherein $R^1$ is hydroxy.

3. An oxazolidine as claimed in claim 1 wherein $R^1$ is $R^3O$—.

4. S-3-tert-butyl-5-hydroxymethyloxazolidine.
5. S-2-phenyl-3-tert-butyl-5-hydroxymethyloxazolidine.
6. S-3-tert-butyl-5-(p-toluenesulfonyloxymethyl)oxazolidine.
7. S-3-tert-butyl-5-(p-nitrobenzenesulfonyloxymethyl)oxazolidine.
8. S-3-tert-butyl-5-(p-bromobenzenesulfonyloxymethyl)oxazolidine.
9. An optically active 3-Y-5-hydroxymethyloxazolidine in the sinister configuration wherein Y is a straight or branched chain $C_1$-$C_5$ alkyl or hydroxy substituted straight or branched chain $C_1$-$C_5$ alkyl.
10. S-3-Isopropyl-5-hydroxymethyloxazolidine.
11. S-3-(2,2-dimethylpropyl)-5-hydroxymethyloxazolidine.
12. S-3-(1,1-dimethyl-2-hydroxyethyl)-5-hydroxymethyl oxazolidine.
13. An optically active 2- $C_1$-$C_3$ alkyl-3-Y-5-hydroxymethyloxazolidine in the sinister configuration wherein Y is a straight or branched chain $C_1$-$C_5$ alkyl or hydroxy substituted straight or branched chain $C_1$-$C_5$ alkyl.
14. S-2-isopropyl-3-tert-butyl-5-hydroxymethyloxazolidine.
15. An optically active 2-aryl-3-Y-5-hydroxymethyloxazolidine in the sinister configuration wherein aryl is phenyl optionally having 1 to 3 substituents selected from the group consisting of
   a. 1-3 bromo groups,
   b. 1-3 chloro groups,
   c. 1-3 methyl groups,
   d. 1-3 hydroxy groups,
   and
   e. a methoxy group
and Y is a straight or branched chain $C_1$-$C_5$ alkyl or hydroxy substituted straight or branched chain $C_1$-$C_5$ alkyl.
16. An optically active 3-Y-5-($C_{1-16}$alkylsulfonyloxymethyl)oxazolidine in the sinister configuration wherein Y is a straight or branched chain $C_1$-$C_5$ alkyl or hydroxy substituted straight or branched chain $C_1$-$C_5$ alkyl.
17. An optically active 3-Y-5 benzene-or substituted benzenesulfonyloxymethyl oxazolidine in the sinister configuration wherein said benzene substituents are selected from the group consisting of
   a. an amino group,
   b. 1-3 bromo groups,
   c. 1-3 chloro groups,
   d. a chloro and a nitro group,
   e. a fluoro group,
   f. a methoxy group,
   g. 1-3 methyl groups
   and
   h. a nitro group,
and Y is a straight or branched chain $C_1$-$C_5$ alkyl or hydroxy substituted straight or branched chain $C_1$-$C_5$ alkyl.

* * * * *